United States Patent [19]

Barthel

[11] 4,397,316
[45] Aug. 9, 1983

[54] RATE AND A-V DELAY GENERATOR FOR HEART PACEMAKER

[75] Inventor: Thomas C. Barthel, Becker, Minn.

[73] Assignee: Medtronic, Inc., Minneapolis, Minn.

[21] Appl. No.: 189,306

[22] Filed: Sep. 22, 1980

Related U.S. Application Data

[63] Continuation of Ser. No. 25,654, Mar. 30, 1979, abandoned.

[51] Int. Cl.³ .............................................. A61N 1/36
[52] U.S. Cl. ............................................ 128/419 PG
[58] Field of Search ................................ 128/419 PG

[56] References Cited

U.S. PATENT DOCUMENTS

| | | | |
|---|---|---|---|
| 3,534,245 | 10/1970 | Limberg | 323/4 |
| 3,555,305 | 1/1971 | Luczkowski | 307/265 |
| 3,558,924 | 1/1971 | Lindell | 307/260 |
| 3,593,718 | 7/1971 | Krasner et al. | 128/419 PG |
| 3,656,487 | 4/1972 | Gobeli | 128/419 PG |
| 3,757,791 | 9/1973 | Berkovits | 128/419 P |
| 3,768,486 | 10/1973 | Berkovits | 128/419 PG |
| 3,783,878 | 1/1974 | Thaler et al. | 128/419 P |
| 3,972,334 | 8/1976 | Wickham | 128/419 PG |
| 3,985,142 | 10/1976 | Wickham | 128/419 PG |
| 4,091,817 | 5/1978 | Thaler | 128/419 PG |

FOREIGN PATENT DOCUMENTS 1953760 3/1971 Fed. Rep. of Germany ...... 307/260

OTHER PUBLICATIONS

The Electronic Engineer, vol. 30, No. 1, Jan. 1971, p. 41, Radnor, U.S.A.
M. Strange: "Op Amps Give Mutually-Exclusive Digital Sequencing".
Electronics, vol. 49, No. 17, Aug. 19, 1976, p. 94, New York, U.S.A.
N. G. Wheelock: "Micropower Comparators Generate 2-Phase Clock".
Electronic Design, vol. 17, No. 11, May 24, 1969, p. 102, Rochelle Park, U.S.A.
Chauvin: "Get Emitter-Follower Action Without Input/Output Level Shift".
Electronics, vol. 47, No. 23, Nov. 14, 1974, p. 127, New York, U.S.A.
Delagrange: "As Clipper, IC Comparator is Improved by Feedback".

Primary Examiner—William E. Kamm
Attorney, Agent, or Firm—Merchant, Gould, Smith, Edell, Welter & Schmidt

[57] ABSTRACT

A generating circuit for producing atrial and ventricular timing signals for a pacemaker which allows independent control of ventricular rate and atrial-ventricular delay. A voltage ramp signal is generated and compared to a reference voltage signal by a voltage comparator which produces an output signal when the ramp voltage reaches the reference voltage. A second voltage comparator compares the reference voltage with a second ramp voltage signal which is generated by offsetting the first voltage ramp signal so that the second ramp signal parallels and leads the first voltage ramp signal by an offset voltage difference. The second voltage comparator produces a second output signal when the second ramp voltage signal equals the reference voltage. Alternatively, the second output signal can be produced by offsetting the reference voltage signal and comparing it to the voltage ramp signal in the second comparator. The first and second output signals provide atrial and ventricular timing signals. The ventricular rate is controlled by adjusting the relationship of the reference voltage and the first voltage ramp signal. The atrial-ventricular delay is independently controlled by adjusting the amount of the offset voltage.

14 Claims, 2 Drawing Figures

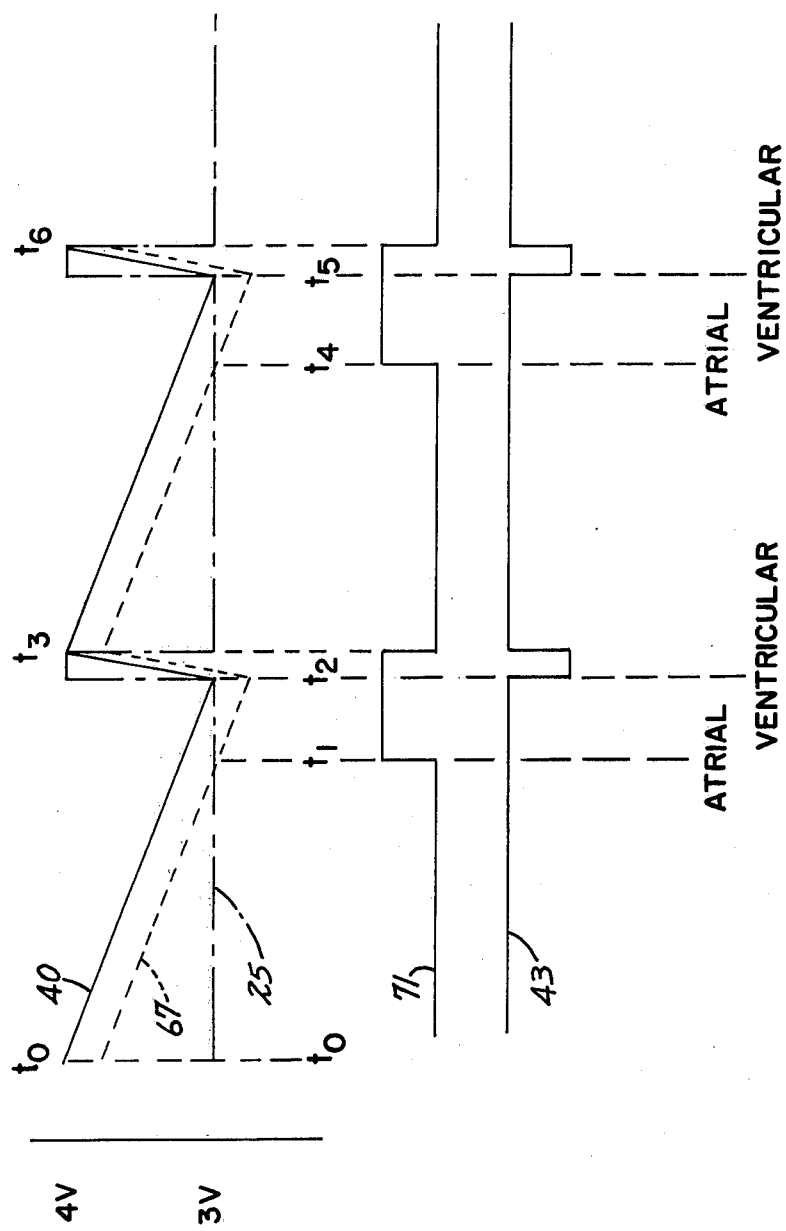

RATE AND A-V DELAY GENERATOR FOR HEART PACEMAKER

This application is a continuation of application Ser. No. 25,654, filed Mar. 30, 1979 now abondoned.

TECHNICAL FIELD OF THE INVENTION

The present invention pertains to the field of artificial heart pacemakers, and more particularly to generating circuits for providing the timing pulses for atrial and ventricular stimulation pulses in an Atrial-Ventricular (A-V) sequential pacemaker. More specifically, the present invention pertains to an improved rate and A-V timing generator that permits rate and A-V delay interval to be independently adjusted by their own separate controls, which controls have no substantial interaction with each other.

BACKGROUND OF THE PRIOR ART

It is generally necessary to provide some means for adjusting the pacing rate in an artificial heart pacemaker so as to tailor the operation of the device to the needs of the patient. In the case of an A-V sequential pacemaker, it is also generally necessary to provide some means for adjusting the delay interval between the atrial and ventricular stimulation pulses. Implantable pacemakers present their own problems in achieving these adjustment functions, and numerous techniques have been developed in the prior art to meet these needs. In the case of external heart pacemakers, in which the generating and control circuitry is in a device external of the body connected by electrode leads which pass through the skin to the patient's heart, control of pacing rate, A-V delay and possibly other operating parameter is generally accomplished by control knobs on the front panel of the device. Through the use of these controls the physician can adjust the timing parameters of the pacemaker to meet the patient's needs. However, external A-V sequential pacemakers in the prior art are subject to certain unwanted interactions between the control for rate and the control for A-V delay, in that changing the control knob setting for one control not only changes the intended timing function, but also causes an unwanted change in the other parameter.

It has long been recognized in the prior art that the basic heart beat rate to be maintained by an A-V pacemaker must be with reference to the ventricular beats, either spontaneous or stimulated, and not by reference to the atrial stimulation. This has caused certain complications in the design of satisfactory rate and A-V delayed generating circuits. If it were possible simply to reference basic rate to the atrial pulses, it would be a simple matter to provide circuits to time out a first interval for the atrial-to-atrial rate, and a second shorter interval following an atrial pulse to provide the A-V delay interval, and the two time intervals could easily be independently controllable. However, it has been recognized that such a system would lead to variable or erratic heart rate, because of the uncertainty in practice as to whether the ventrical may depolarize following a stimulated atrial depolarization but before the pacemaker would provide a ventricular stimulation output pulse. Since this situation can change from beat to beat, the time interval between successive ventricular depolarizations would vary by a certain amount under such a system, and this variation would not be acceptable.

Accordingly, generating circuits have been designed in the prior art to control the basic heart rate according to the ventricular depolarizations, either spontaneous or stimulated, while providing means for generating the atrial stimulation pulse at the proper time interval prior to the ventricular pulse. Generally these systems have used a wave or ramp generating circuit and a pair of variable voltage divider references, one for the atrial pulse and one for the ventricular pulse. Obviously, changing the control for the ventricular repetition rate completely changes the A-V interval, which would necessitate readjustment and monitoring of both quantities each time one was to be changed. To minimize this problem, it has been proposed in the prior art to use a pair of precision ganged potentiometers having a fixed resistance difference between them to operate both references simultaneously for rate, with a separate control for interval. However, prior art devices according to this approach are subject to the disadvantages of the relatively high cost of precision potentiometers and inaccuracies resulting from even slight mismatching of the precision potentiometers.

The present invention solves these and other problems by providing an improved rate and A-V delay generator in which the separate controls for ventricular rate and A-V delay interval are independent and have no unwanted couplings or interferences with each other's operation. This permits the physician to operate one control knob to vary the rate, while having no effect upon the A-V delay interval; and to adjust the delay knob to control the A-V delay while having no effect upon the basic ventricular rate. The independence of these controls results in quicker and easier adjustments by the physician with less chance of error. This independent adjustment feature is achieved accurately, efficiently, and without the cost and accuracy problems associated with matched potentiometers.

SUMMARY OF THE INVENTION

The present invention provides an improved generating circuit for producing atrial and ventricular timing signals for a pacemaker with independent control of ventricular rate and atrial-ventricular delay. The invention includes means for generating a voltage ramp signal, means for providing a reference voltage, and voltage comparison means for producing an output signal when the ramp voltage reaches the reference voltage. Voltage offset means are provided to receive the voltage ramp signal and produce a second voltage ramp signal which parallels and leads the first ramp signal by an offset voltage difference. A second voltage comparison means compares the second voltage ramp to the reference voltage and provides a second output signal which is spaced in time from said first output signal by an amount depending on the amount of the offset voltage. Alternatively, the first voltage ramp can be applied to both comparators, and the voltage offset means can be connected to the reference voltage to provide a second reference voltage which differs from the first reference voltage by the offset amount. This second reference voltage can then be applied to the second voltage comparison means. In either case, means are provided for adjusting the amount of the offset voltage, whereby the earlier and later of said output signals, respectively, provide atrial and ventricular timing signals, and whereby the ventricular rate may be controlled by adjusting the relationship of the reference voltage and the first voltage ramp signal, and atrial-ventricular delay may be independently controlled by adjusting the amount of the offset voltage.

According to a preferred embodiment, the voltage offset means includes a diode network connected to provide a predetermined voltage drop as the offset voltage, and a variable resistor in parallel therewith can be provided to select an adjustable portion of the voltage drop. In a preferred embodiment, an additional Zener diode is included in the network to stabilize the predetermined voltage drop.

BRIEF DESCRIPTION OF THE DRAWING

FIG. 2 shows pertinent waveforms illustrating the operation of the circuit of FIG. 1.

DETAILED DESCRIPTION OF THE PREFERRED EMBODIMENTS

Figure 1:
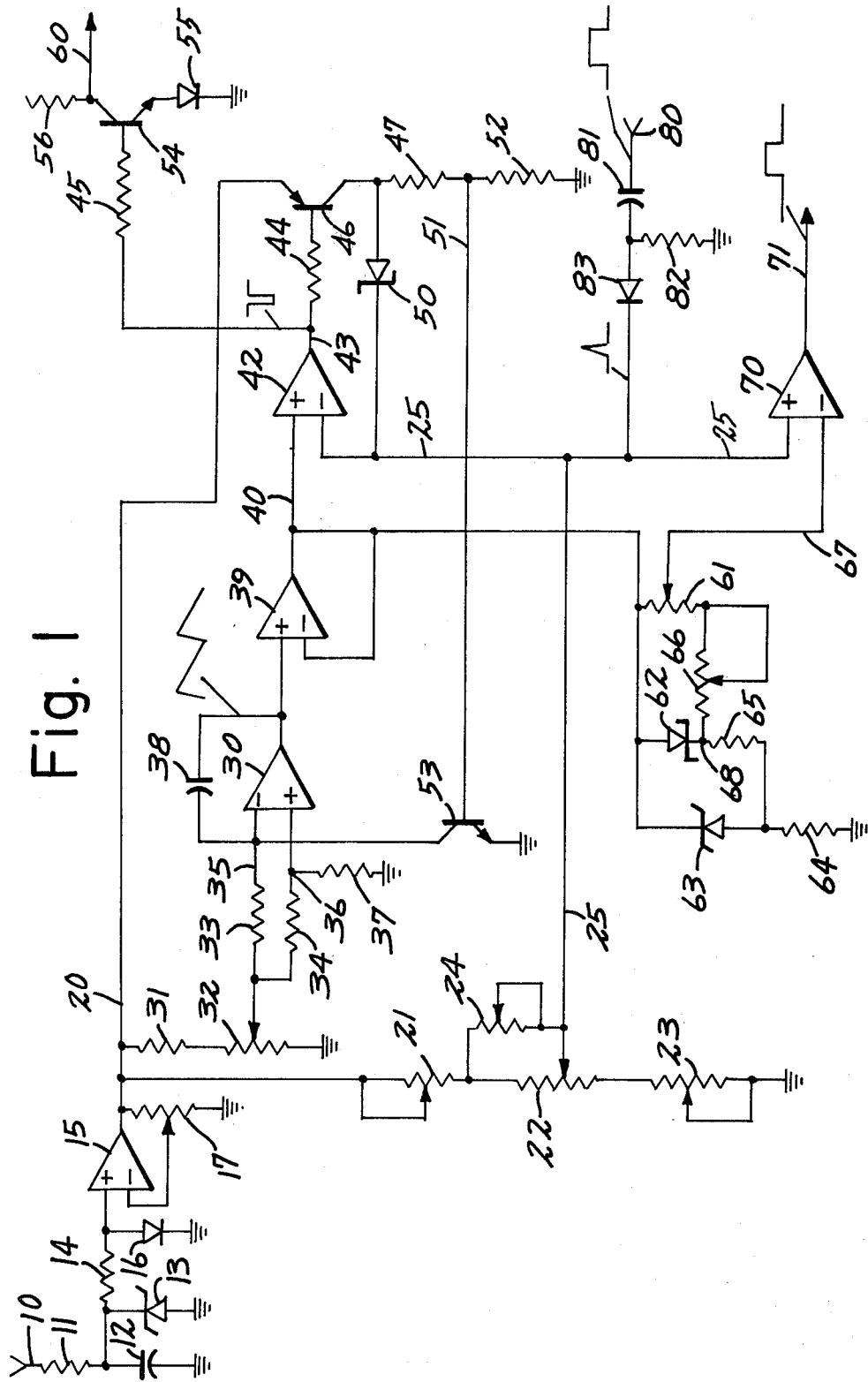
FIG. 1 shows an electrical schematic diagram of the preferred embodiment of the invention.

In the circuitry shown in FIG. 1, conductor 10 is intended for connection to the battery or other power source of the pacemaker, but this battery or power source is not shown in FIG. 1. Conductor 10 connects to resistor 11, the other side of which connects to capacitor 12, the cathode of Zener diode 13, and resistor 14. The anode of diode 13 and the other side of capacitor 12 are connected to signal ground. The other side of resistor 14 connects to the non-inverting input of an operational amplifier 15. A diode 16 also connects from this input to signal ground. The output of operational amplifier 15 is connected to conductor 20. A potentiometer 17 connects from conductor 20 to signal ground, and the variable terminal of potentiometer 17 connects to the inverting input of operational amplifier 15. Operational amplifier 15 and associated components provide a reference voltage on conductor 20 as is described more fully hereinafter.

Potentiometers 21, 22, and 23 are connected in series between conductor 20 and signal ground to form a variable voltage divider. The variable tap of potentiometer 21 and its upper end of FIG. 1, are connected to a branch of conductor 20, so that potentiometer 21 provides a trimmer adjustment function. In similar fashion, the variable tap of potentiometer 23 is tied to signal ground together with the lower side of potentiometer 23 in FIG. 1, to form a trimmer resistor. The variable tap of potentiometer 24, 22 connects to a conductor 25, and a further potentiometer, used as a trimmer, is connected between conductors 25 and the junction between potentiometers 21 and 22. The variable tap of potentiometer 24 is connected to conductor 25 and the variable tap of potentiometer 22.

Resistor 31 and potentiometer 32 are connected in series between conductor 20 and signal ground to form a variable voltage divider. The variable tap of potentiometer 32 connects to a pair of resistors 33 and 34. The other side of resistor 33 connects to conductor 35, and the other side of resistor 34 connects to a conductor 36. Conductor 35 connects to the inverting input of an operational amplifier 30, and in similar manner conductor 36 connects to the non-inverting input thereof. A resistor 37 connects from conductor 36 to signal ground. A capacitor 38 connects from the output of amplifier 30 to its inverting input at conductor 35. The output of amplifier 30 also connects to the non-inverting input of a further operational amplifier 39, whose output connects to conductor 40, a branch of which feeds back to the inverting input of amplifier 39. Amplifier 39 connected in this fashion serves only as a unity gain amplifier which performs no logical or wave shaping function. However, it has been found desirable to use amplifier 39 as a buffer amplifier, when amplifier 30 and the operational amplifiers in the circuit are starved for current. In the preferred embodiment, in order to minimize battery drain, the operational amplifiers are connected to the battery through current limiting resistors (not shown) so that they operate at only approximately 30 microamps of current. The use of buffer amplifier 39 is desirable in this situation in order to eliminate unwanted coupling effects among the amplifiers.

Conductor 40 connects to the non-inverting input of an operational amplifier 42, which is operated open loop as a voltage comparator. The inverting input of amplifier 42 is connected to a branch of conductor 25. The output of amplifier 42 connects to a conductor 43, which in turn connects to resistors 44 and 45. Resistor 44 connects to the base of a PNP transistor 46, whose emitter connects to conductor 20, and whose collector connects to a resistor 47 and the anode of a Schottky diode 50. The cathode of diode 50 connects to a branch of conductor 25. The other side of resistor 47 connects to a conductor 51, and to a resistor 52, the other side of which connects to signal ground.

Conductor 51 connects to the base of a NPN transistor 53, whose emitter connects to signal ground, and whose collector connects to conductor 35 at one of the inputs of amplifier 30.

An optional output circuit may be connected to conductor 43. This optional circuit consists of an NPN transistor 54, whose base connects through resistor 45 to conductor 43, whose emitter connects through diode 55 to signal ground, and whose collector connects through resistor 56 to the battery or other source of power (not shown). An output may be taken from conductor 60, at the collector of transistor 54.

A branch of conductor 40 connects to a potentiometer 61, the anode of a Schottky diode 62, and the cathode of a Zener diode 63. The anode of diode 63 connects through resistor 64 to signal ground, and also through resistor 65 to the cathode of Schottky diode 62 at conductor 68. Potentiometers 61 and 66 are connected in series between conductor 40 and conductor 68. The variable tap of potentiometer 66 is connected to one end thereof so as to make a resistance trimmer control, and the variable tap of potentiometer 61 connects to a conductor 67.

An operational amplifier 70, operated open loop as a voltage comparator, receives a branch of conductor 25 at its non-inverting input, and receives conductor 67 as its inverting input. The output of comparator 70 provides an output of the system at conductor 71.

A terminal 80 is provided for receiving a pulse from the output of the sense amplifier (not shown) of the pacemaker if it is a demand-type pacemaker. Terminal 80 connects through capacitor 81 to a resistor 82, which also connects to signal ground, and to the anode of a diode 83. The cathode of this diode connects to a branch of conductor 25.

In operation, amplifier 15 and associated components provide a reference voltage at conductor 20 which is used by the other circuits of FIG. 1. Resistor 11 limits the current to Zener diode 13, which establishes a reference voltage. In practice, resistor 11 is chosen high enough to starve Zener 13 for current. Capacitor 12 is provided for filtering purposes. The voltage established by diode 13 is fed through resistor 14 to diode 16, whose forward bias drop establishes an input voltage level for amplifier 15. The feedback voltage is adjusted by potentiometer 17 so that any desired reference output voltage, within the capabilities of amplifier 15 and the limitations of the applied battery voltage, can be provided at conductor 20. In the preferred embodiment, a stable reference voltage of 4 volts is provided at conductor 20. The biasing and filtering components just described at the input of amplifier 15 provide a very stable reference which is independent of noise or fluctuations in the battery caused by the switching or operation of other circuits of the pacemaker.

The voltage divider consisting of resistances 21, 22, and 23 is used to establish a reference voltage at conductor 25. Potentiometer 22 is mounted on the front panel, and it is the rate control for the circuit. Potentiometer 21 is used to limit the maximum rate, while potentiometer 23 may be used to establish the minimum rate. Potentiometer 24 is used to trim the response of potentiometer 22, to provide a desired nonlinear effect for its operation. The voltage selected by potentiometer 22 and applied to conductor 25 is used as a comparison voltage for comparators 42 and 70.

Potentiometer 32 is used to adjust an input current to the inverting input of amplifier 30. Except for reset operation described below, transistor 53 is normally off, and the current applied to conductor 35 through resistor 33 must be matched by charging current for capacitor 38, providing a decreasing ramp voltage as suggested by the waveform at the output of amplifier 30 in FIG. 1. In other words, the capacitor feedback connection for amplifier 30 provides an integrator function in response to the voltage applied from potentiometer 32. The network including resistors 34 and 37 adjusts the gain of the amplifier. Potentiometer 32 adjusts the slopes of the ramp.

The decreasing ramp voltage from amplifier 30 is applied through buffer 39 to the non-inverting input of comparator 42. Initially, this voltage is higher than the voltage at conductor 25, resulting in a logical high output at conductor 43. When the voltage on the descending ramp from amplifier 30 drops below the voltage at conductor 25, comparator 42 changes states, as indicated by the waveform at conductor 43. The ground or logical low signal at this point turns on transistor 46, and this in turn results in the application of the reference voltage from conductor 20 through transistor 46 and diode 50 to conductor 25, pulling the voltage at conductor 25 up to the reference voltage, less the small drops through transistor 46 and diode 50. A Schottcky diode is used at this location because of its low forward bias voltage drop.

The turn on of transistor 46 also causes the turn on of transistor 53, causing reset of the voltage ramp generator by providing a discharge path for capacitor 38 to ground. As this discharge occurs, the voltage at the output of amplifier 30 rises rapidly in a very short but finite time interval during the discharge of capacitor 38. This rise continues until the voltage waveform at conductor 40 exceeds the reference voltage being applied thereto through diode 50. During the reset interval, the reference voltage applied through diode 50 overrides the voltage set by potentiometer 22. This voltage reference again is only a few tenths of a volt lower than the reference voltage at conductor 20, and typically is somewhat higher than the voltage that would otherwise be set on conductor 25 by potentiometer 22. When the rising waveform at conductor 40 exceeds the reference voltage at conductor 25, comparator 42 again changes state, terminating the reset pulse. Transistor 46 is then turned off, turning off transistor 53 and removing the forward bias for diode 50. The voltage at conductor 25 then returns to that which was set by potentiometer 22, and amplifier 30 begins another descending ramp waveform.

It will thus be seen that the ramp generated by amplifier 30 has a starting voltage determined by the voltage reference at conductor 20 (minus voltage drops through transistor 46 and diode 50), a lower voltage limit determined by the voltage on conductor 25 as determined by the settings of the voltage divider that includes potentiometer 22, and a slope in terms of volts per seconds which can be controlled by the setting of potentiometer 32.

While the ramp voltage at conductor 40 is applied to comparator 42, the same waveform but minus an offset voltage is applied by conductor 67 to comparator 70. The offset voltage is provided by Schottcky diode 62 and associated components as follows. The voltage at conductor 40 appears at conductor 68 minus the forward bias voltage drop of Schottcky diode 62, which is approximately 0.3 volt. The waveform at conductor 68 thus is an image of the waveform at conductor 40, except that it is at all times disadvantaged by the forward bias drop of diode 62. This drop is relatively constant, and is stabilized further by the use of Zener diode 63. This is, in the preferred embodiment, a 1.8 volt Zener, but it is starved for current and is therefore running at a lower voltage. The use of this diode helps stabilize the applied voltage and improve the accuracy of this portion of the circuit.

The desired portion of the reduced or disadvantaged waveform of conductor 68 is selected by adjusting potentiometers 61 and 66. Potentiometer 61 is a front panel control for the atrial-ventricular delay interval. Potentiometer 66 is a trimmer used to set the maximum allowed A-V interval. When potentiometer 61 is set with its variable tap electrically closest to conductor 40, the voltage at conductor 67 will be identical to the voltage at conductor 40. As potentiometer 61 is adjusted away from that position, the voltage at conductor 67 reflects an increasing amount of the voltage offset or disadvantage which is provided by diode 62, with the maximum offset being provided when potentiometers 61 and 66 are adjusted to obtain the full forward bias voltage drop of diode 62.

The overall operation of the circuit of FIG. 1 in providing atrial and ventricular timing pulses for a pacemaker is best understood with the aid of the waveforms of FIG. 2. The vertical axis represents voltage and the horizontal axis represents time. The various waveforms are identified by reference members which are the same as the corresponding points in the circuit of FIG. 1 at which the waveforms are found. Thus, waveform 40 represents the voltage ramp at conductor 40 of FIG. 1, etc.

For the example of FIG. 2, assume that the reference voltage at conductor 20 is at near 4 volts, and potentiometer 22 has been adjusted to provide a reference of approximately 3 volts. During the interval from time $t_0$ to $t_1$, waveform 40 decreases at a uniform rate. Waveform 67 decreases at the identical rate, but waveform 67 is displaced downwardly at each point from waveform 40 by the amount of offset provided by diode 62, potentiometer 61 and associated components. In the example shown, the amount of offset is approximately 0.25 volts.

At time $t_1$, voltage waveform 67 decreases below the 3 volt reference on conductor 25, causing comparator 70 to change states, and at this time, waveform 71 switches to a logical high.

Waveforms 40 and 67 continue on their decreasing ramp until at time $t_2$ the voltage at conductor 40 reaches the reference voltage at conductor 25. This causes comparator 42 to change status and waveform 43 switches to a logical low level. At the same time transistor 46 turns on and the reference voltage from conductor 20 is applied through diode 50 to conductor 25, causing it to jump upward to the reference voltage of 4 volts (saturation voltage drop for transistor 46 and forward bias voltage drop for diode 50 have been omitted for clarity). At the same time transistor 53 is turned on to discharge capacitor 38 and reset generator 30, this taking the short but finite time interval from $t_2$ to $t_3$. At time $t_3$ waveform 40 reaches the reference voltage for 4 volts applied through diode 50, causing comparator 42 to change states to its high logical level, turning off transistors 46 and 53. This returns the 3 volt reference set by potentiometer 22 to conductor 25 thus causing comparator 70 to change states, returning to a logical low level at time $t_3$. With the turn off of transistor 53, the ramp generator is released to begin another cycle.

The cycle is thus repeated with waveform 71 again changing states at time $t_4$, waveform 43 changing states at time $t_5$, and a new descending ramp again at time $t_6$.

The leading edges of the pulses of waveform 71 provide the triggering signals for atrial stimulation. The leading edges of the pulses on waveform 43 at $t_2$, $t_5$ may provide the triggering signals for ventricular stimulation. Thus, logic circuits as are generally know in the art can connect from conductors 71 and 60 of FIG. 1 to the atrial and ventricular stimulating pulse circuits respectively of the pacemaker to provide the necessary atrial and ventricular pulses. Alternatively, the trailing edge of the pulse of waveform 43 can be used for the ventricular timing pulse, since in practice $t_2$ and $t_3$ are very closely spaced compared with the $t_1$-$t_2$ interval. The width of the pulse on waveform 43 is very narrow, and it has been somewhat exaggerated in FIG. 2 for purposes of clarity of explanation.

Consideration of the circuit of FIG. 1 and the waveforms of FIG. 2 will show the manner in which independent adjustment is provided of the A-V delay and the pacing rate, referenced from the ventricular output. Adjustment of potentiometer 22 has the effect of adjustment of the vertical position voltage reference 25 (the portion from time $t_0$ to $t_2$, etc.) and this in turn has the effect of controlling the horizontal or time occurrence of time $t_3$ which defines the ventricular output pulse. Specifically, lowering the voltage at potentiometer 22 increases the interval, or decreases the rate, and vice versa.

The A-V delay interval defined by $t_2$-$t_1$, etc., is determined solely by the slope of waveforms 40 and 67, which are constant and equal, and the offset between these waveforms which is controlled by potentiometer 61. As this offset is decreased, time $t_1$ moves closer to time $t_2$ thus narrowing the pulse of waveform 71, and reducing A-V delay. Increasing the offset has the opposite effect. Adjustment of potentiometer 61 to control the offset has no effect upon the time or horizontal positioning of the events at time $t_2$ or $t_3$, so independence of control action is achieved.

In demand-type pacemakers reset of the pacemaker circuit is effected if a spontaneous beat takes place prior to the time for generation of an output stimulating pulse. Demand-type pacemakers have sensing amplifiers which respond to the R-wave of the heat indicating occurrence of a ventricular depolarization. Terminal 80 of FIG. 1 connects to receive a rectangular output pulse from a sense amplifier as is generally known in the prior art in the event of a ventricular depolarization. This rectangular pulse is differentiated by capacitor 81 and resistor 82, and rectified by diode 83 to appear as a spike at conductor 25. Occurrence of such a spike at any time causes comparator 42 to change states and latch itself via transistor 46 and diode 50 while the ramp generator 30 is reset to the top of its waveform, at which point a new timing cycle is initiated. Thus, occurrence of a ventricular depolarization at any time during the timing cycle will interrupt the timing cycle and restart it. In practice the value of capacitor 81 is selected so that the spike transmitted through diode 83 is just enough to trigger and latch amplifier 42. If capacitor 81 is too large, it could produce the unwanted effect of driving the voltage at conductor 25 above the reference voltage at conductor 20.

By way of example, the circuit component values for a preferred embodiment of the invention, designed to operate from a 9 volt battery source are as follows:

Resistors:
  R11—120 Kilohm
  R14—22 Kilohm
  R17—1 Megohm potentiometer
  R21—100 Kilohm potentiometer
  R22—70 Kilohm potentiometer
  R23—1 Megohm potentiometer
  R24—5 Kilohm potentiometer
  R31—100 Kilohm
  R32—100 Kilohm potentiometer
  R33—51 Kilohm
  R34—24 Kilohm
  R37—24 Kilohm
  R44—10 Kilohm
  R45—2.2 Megohm
  R47—100 Kilohm
  R50—100 Kilohm
  R52—30 Kilohm
  R61—70 Kilohm potentiometer
  R64—200 Kilohm
  R65—51 Kilohm
  R66—200 Kilohm potentiometer
  R82—100 Kilohm Capacitors:
  C12—optional, as required for filtering
  C38—10 mfd
  C81—0.01 mfd Operational Amplifiers: 8021, with current set resistors of 1.5 Megohm.

Transistors:
  46—2N2907
  53—2N3700
  54—2N3700

Diodes:
  D13—IN4678
  D16—IN4148
  D50—IN5711
  D55—IN4148
  D62—IN5711
  D63—IN4678
  D83—IN4148.

While the preferred embodiment has been shown with a negative-going ramp, the invention could of course easily be implemented with a positive-going ramp by suitable changes in polarities of components. Also, it will be appreciated that the invention can also be implemented by applying the ramp voltage directly to both voltage comparators, and by connecting the voltage offset network which includes diode 62 to the reference voltage from conductor 25. The network would then produce a second or offset reference voltage which could be fed to one of the comparators (comparator 42 for the polarities shown in FIG. 1) and the original reference voltage from lead 25 would go to the other comparator. Either way the two comparators would trigger at times spaced apart according to the amount of the offset voltage, to define the A-V delay interval.

As pointed out in the foregoing description, the present invention provides an improved rate and A-V delayed generator for a pacemaker, in which the controls for ventricular rate and A-V delay are independent of each other, and have no unwanted couplings of interactions.

What is claimed:

1. Apparatus for producing atrial and ventricular timing signals for a pacemaker with independent control of ventricular rate and atrial-ventricular delay, comprising:
means for generating first and second voltage signals, one of said voltage signals comprising a voltage ramp signal and the other of said voltage signals comprising a reference voltage;
first voltage comparison means connected to receive said first and second voltage signals and operative to produce a first output signal when said voltage ramp signal reaches a predetermined relationship with said reference voltage;
voltage offset means connected to receive one of said voltage signals and operative to produce an offset voltage signal which differs therefrom by an offset voltage;
second voltage comparison means connected to receive said voltage offset signal and the other of said voltage signals and operative to produce another output signal when said voltage offset signal and said other voltage signal reach a predetermined relationship, said output signal being spaced in time from said first output signal according to the amount of said offset voltage; and
means for adjusting the amount of said offset voltage, whereby the earlier and later output signals provide atrial and ventricular timing signals, respectively, and whereby the ventricular rate may be controlled by adjusting the relationship of said reference voltage and said voltage ramp signal, and the atrial-ventricular delay may be independently controlled by adjusting the amount of said offset voltage.

2. Apparatus according to claim 1 wherein said voltage offset means is connected to receive said voltage ramp signal and is operative to produce a second voltage ramp signal that parallels and leads said first mentioned voltage ramp signal and differs therefrom by said predetermined offset voltage.

3. Apparatus according to claim 1 wherein said voltage offset means is connected to receive said reference voltage and is operative to produce a second reference voltage that differs therefrom by said predetermined offset voltage.

4. Apparatus according to claim 1 further including means for adjusting said reference voltage to control the ventricular rate.

5. Apparatus according to claim 1 wherein said voltage offset means includes a diode network connected to provide a predetermined voltage drop as the offset voltage.

6. Apparatus according to claim 5 wherein said means for adjusting the amount of said offset voltage includes a variable resistor connected in a circuit parallel to said diode network whereby an adjustable portion of said predetermined voltage drop may be selected as said predetermined offset voltage.

7. Apparatus for producing atrial and ventricular timing signals for a pacemaker with independent control of ventricular rate and atrial-ventricular delay, comprising:
means for generating a voltage ramp signal;
means for providing an adjustable reference voltage;
first voltage comparison means connected to receive said ramp signal and said reference voltage and operative to produce an output signal comprising the ventricular timing signal when said ramp voltage reaches said reference voltage;
voltage offset means connected to receive said voltage ramp signal and operative in response thereto to produce a second voltage ramp signal that paralllels and leads said first mentioned voltage ramp signal and differs therefrom by a predetermined offset voltage;
second voltage comparison means connected to receive said reference voltage and said second voltage ramp signal and operative to produce an output signal comprising the atrial timing signal; and
means for adjusting the amount of said offset voltage;
whereby the ventricular rate may be controlled by adjusting said reference voltage and the atrial-ventricular delay may be independently controlled by adjusting said offset voltage.

8. Apparatus according to claim 7 further including means responsive to said output signal of said first voltage comparison means and operative for resetting said voltage ramp generating means.

9. Apparatus according to claim 7 wherein said voltage offset means comprises a diode network.

10. Apparatus according to claim 7 wherein said voltage offset means comprises a first diode connected to receive said voltage ramp signal and wherein said offset voltage comprises the forward bias voltage drop of the diode.

11. Apparatus according to claim 10 further including a resistor in series with said first diode and a Zener diode connected in parallel therewith, to further stabilize said offset voltage.

12. Apparatus according to claim 11 including a voltage divider connected in parallel with said first diode, and means for picking a selected voltage from said divider for applying to said second voltage comparison means.

13. Apparatus according to claim 12 wherein said voltage divider includes a potentiometer.

14. Apparatus according to claim 11 wherein said first diode comprises a Schottcky diode.

* * * * *